United States Patent
Nollert et al.

(10) Patent No.: US 9,237,926 B2
(45) Date of Patent: Jan. 19, 2016

(54) PAIR OF ENDOCARDIAL AND EPICARDIAL CATHETERS, CATHETER AND METHOD FOR POSITIONING ELECTRODES ON A CARDIAC WALL AND METHOD FOR THE ABLATION OF CARDIAC MUSCLE TISSUE

(75) Inventors: Georg Nollert, Straβlach-Dingharting (DE); Martin Ostermeier, Buckenhof (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 842 days.

(21) Appl. No.: 13/334,104

(22) Filed: Dec. 22, 2011

(65) Prior Publication Data

US 2012/0172872 A1 Jul. 5, 2012

(30) Foreign Application Priority Data

Dec. 23, 2010 (DE) .................. 10 2010 064 101

(51) Int. Cl.
| | |
|---|---|
| A61B 18/14 | (2006.01) |
| A61B 17/00 | (2006.01) |
| A61B 18/00 | (2006.01) |
| A61B 19/00 | (2006.01) |

(52) U.S. Cl.
CPC ... *A61B 18/1492* (2013.01); *A61B 2017/00318* (2013.01); *A61B 2017/00876* (2013.01); *A61B 2018/00273* (2013.01); *A61B 2018/00357* (2013.01); *A61B 2018/00363* (2013.01); *A61B 2018/00577* (2013.01); *A61B 2018/1467* (2013.01); *A61B 2019/2253* (2013.01)

(58) Field of Classification Search
None
See application file for complete search history.

(56) References Cited

U.S. PATENT DOCUMENTS

| | | |
|---|---|---|
| 2008/0188850 A1 | 8/2008 | Berube |
| 2008/0288038 A1 | 11/2008 | Cao |
| 2010/0010488 A1* | 1/2010 | Kassab et al. .................. 606/41 |

FOREIGN PATENT DOCUMENTS

WO WO 2008091610 A2 * 7/2008

* cited by examiner

*Primary Examiner* — Brian T Gedeon
*Assistant Examiner* — Ankit Tejani

(57) ABSTRACT

The ablation of tissue in a cardiac wall is performed by introducing an endocardial catheter into the interior of a heart and an epicardial catheter is placed on the cardiac wall. With the aid of an electromagnet and a counter-element, which can be permanently magnetized or can also be an electromagnet, the two catheters are mutually attracted in such a way that electrodes come into contact with opposite sides of the cardiac wall such that the electrodes are optimally positioned. The use of a catheter with a plurality of such electrodes in a row enables the removal of whole lines of destroyed cardiac wall tissue by ablation.

15 Claims, 3 Drawing Sheets

PAIR OF ENDOCARDIAL AND EPICARDIAL CATHETERS, CATHETER AND METHOD FOR POSITIONING ELECTRODES ON A CARDIAC WALL AND METHOD FOR THE ABLATION OF CARDIAC MUSCLE TISSUE

CROSS REFERENCE TO RELATED APPLICATIONS

This application claims priority of German application No. 10 2010 064 101.4 filed Dec. 23, 2010, which is incorporated by reference herein in its entirety.

FIELD OF INVENTION

The invention relates to the ablation of cardiac muscle tissue and the devices to be used therefor. In this context, ablation should be understood to mean the complete destruction of cells in the cardiac wall. As a result, no further electrical stimuli can be conducted via the destroyed location. This is advisable if the location serves to create or transmit electrical stimuli which cause cardiac arrhythmia.

BACKGROUND OF INVENTION

For the purposes of ablation, a catheter with a unipolar electrode, a so-called endocardial catheter, is introduced into the heart. A large-surface electrode is placed on the patient's skin as a counter-electrode. If the electrodes are supplied with suitably shaped voltage, energy is applied to the cardiac muscle.

The disadvantage of this is that the target is not always hit accurately and instead surrounding tissue can be damaged by the electrical energy.

It is known from cardiosurgery to use forceps-like devices for ablation with two cheeks with one of these cheeks being introduced through a hole in the atrial wall of the heart. The cardiac wall is then clamped between the cheeks before a defined energy is fed through the cheeks.

This method from cardiosurgery is precise, but requires the thorax of the patient to be opened up.

SUMMARY OF INVENTION

The object of the invention is to disclose a method for performing improved ablation and simultaneously to provide the technical apparatuses required for this.

The object is achieved by a catheter pair, a catheter, a method for positioning electrodes on a cardiac wall, and a method for the ablation of cardiac wall tissue as claimed in the claims.

According to the invention, therefore, a pair consisting of a catheter for endocardial use (endocardial catheter) and a catheter for epicardial use (epicardial catheter) each with an electrode is provided, wherein one of the catheters comprises an electromagnet and the other catheter comprises a counter-element that can be attracted by the electromagnet.

In this way, the endocardial catheter can be placed in the heart, the catheter for epicardial use is placed on the outside of the cardiac wall. If the electromagnet on one of the catheters is then excited, the counter-element is attracted and the catheters clamp the cardiac wall between them. On guidance by a suitable locating system or under control with the aid of imaging, in this way the two electrodes can be positioned precisely at the correct location to be ablated.

This functions particularly precisely if the electromagnet and the counter-element are positioned in such a way that, upon attraction of the counter-element by the electromagnet, the electrodes are brought into adjacency (through the cardiac wall) with each other. This functions to a quite particular degree if the electromagnet and the counter-element are each positioned on the respective catheters such that, upon attraction of the counter-element by the electromagnet through the wall of the heart, the electrodes come to lie on opposite sides of the wall so that a line connecting the electrodes passes through the wall substantially vertically (from 80° to 90°).

These measures can in particular be achieved in that, on one of the catheters, the electromagnet has the same relative position to the electrode on the same catheter as the counter-element on the other catheter to the electrode on the same other catheter. The relative position can in particular be defined by a specific distance, however, it can in particular also relate to a main body on which the elements electromagnet, counter-element and electrodes are mounted. In particular, if both catheters comprise a main body of the same shape, the electrodes should both be arranged at the same location and the electromagnet should be arranged at the same location as the counter-element.

A ferromagnetic metal part is particularly suitable as a counter-element. This can be soft magnetic so that, upon excitation by the electromagnet, it is magnetized for a short time. However, preferably, the ferromagnetic metal part is permanently magnetized, and can then be attracted particularly successfully.

Alternatively, the counter-element can also be an electromagnet, which is then excited in exactly the same way as the other electromagnet.

In a preferred embodiment, at least one of the catheters comprises a plurality of electrodes. If a catheter is provided with a plurality of electrodes, the individual electrodes can be supplied in succession with electrical potential and the sequence of electrodes then produces a sequence of ablation sites in the cardiac wall. This enables, in particular, the provision of a smooth line of ablated tissue, which is particularly desirable to prevent the transmission of electrical stimuli.

Preferably, a plurality of the electrodes, in particular each of the plurality of electrodes, is hereby assigned an electromagnet or a counter-element on the respective other catheter. In this way, electrode after electrode can be brought into adjacency with a counter-electrode as required for precision in the production of a smooth line of ablation tissue.

In a preferred embodiment of the catheter pair according to the invention, the two catheters are connected to the same voltage source. A catheter pair of this kind is, in particular, particularly ready for operation.

The catheter according to a further aspect of the invention, which is preferably also the catheter for epicardial use of the catheter pair, comprises a tube-shaped main body and a plurality of units along this tube shape, that is along the main body, wherein the units each comprise an electrode and an electromagnet. The tube shape causes the electrodes to form a line with the electromagnet. With the aid of a second catheter, which only requires an electrode and a counter-element, but can also comprise a plurality of electrode-counter-element pairs, it is then possible to create a particularly smooth line of ablated tissue in a cardiac wall. The catheter for epicardial use in particular comprises a plurality of main bodies, which are coupled to each other by at least one cable in such a way and have such a shape that that pulling on the cables results in a curved shape of the catheter. The shape of the main body has, in particular, a trapezoidal cross section or is shorter on one side than the other side in some other way so that a curved shape of the catheter can result when the main bodies are brought into contact with each other.

The method according to the invention for positioning electrodes on a cardiac wall consists in the insertion of an endocardial catheter with an electrode into the heart and the positioning of an epicardial catheter with an electrode on the cardiac wall. Then, with the aid of a magnetic field, a mutual attraction is established with respect to the catheters. The magnetic field can in particular be generated by an electromagnet arranged on one of the catheters.

With the method according to the invention, the electrodes are optimally positioned to facilitate the ablation. However, the positioning can also be used for purposes other than ablation or performed on an electrode other than that which is later to effect the ablation.

With the method according to the invention for the ablation of cardiac muscle tissue, the method for positioning according to the invention is performed initially and subsequently voltage is applied to the two electrodes so that these and the intermediate cardiac wall tissue are supplied with current. The current flowing through the cardiac wall then destroys the cells.

Preferably, at least one of the catheters is the catheter according to the invention with the plurality of units. If the one electrode is attracted into the adjacency of another electrode, which is not disposed at the edge, the two electrodes disposed directly opposite each other are supplied with current initially, and in a next step, the two electrodes from the adjacent unit along the tube shape are supplied with electrical potential so that then the current to the counter-electrode can flow diagonally through the cardiac wall tissue. With a relative position of the two catheters, this enables a larger area of the cardiac wall to be ablated.

This can be performed with the aid of a suitable control device comprising a voltage source, wherein the voltage can then be applied according to a time synchronization in succession between a first connection and a second connection, then between the first connection and a third connection and then between a first connection and a fourth connection, wherein the first connection belongs to the one catheter and the second to fourth connections are provided for the other catheter with the plurality of units.

BRIEF DESCRIPTION OF THE DRAWINGS

The following describes a preferred embodiment of the invention in more detail with reference to the drawing.

DETAILED DESCRIPTION OF INVENTION

Figure 1:
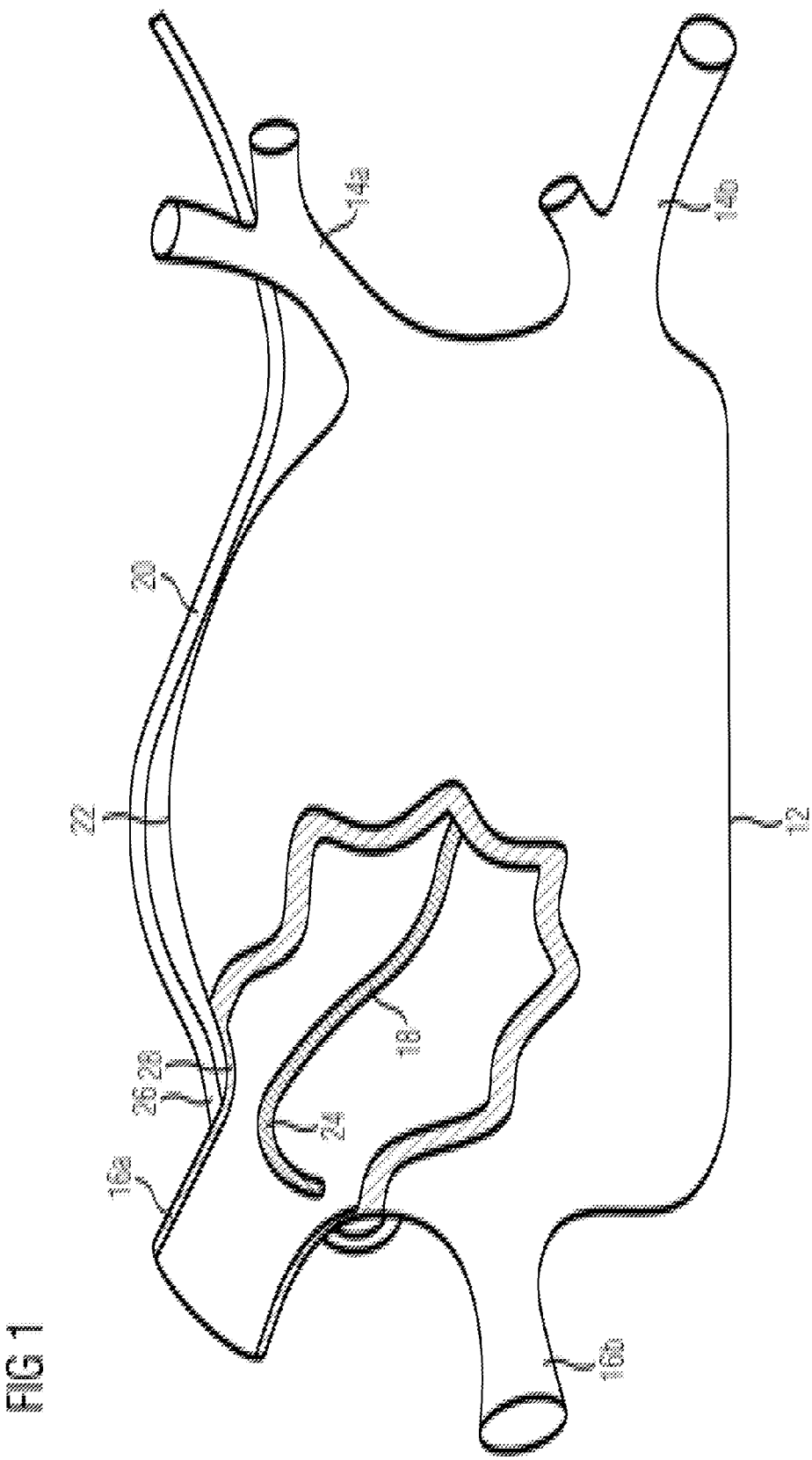
FIG. 1 in perspective view, an atrium of a heart illustrated from the dorsal aspect, wherein the myocardium is partially cut open, showing two catheters used for the ablation of myocardial tissue, FIG. 2 a schematic illustration of a catheter such as that provided according to the invention and FIG. 3 the catheter from FIG. 2 illustrated after its shape has changed.

During an ablation process, tissue is to be destroyed (ablated) locally from the left atrium of a heart. Depicted in addition to the mitral valve 12 are the right upper pulmonary vein 14a, the right lower pulmonary vein 14b, the left upper pulmonary vein 16a and the left lower pulmonary vein 16b. Hereby, the left upper pulmonary vein 16a is shown as cut open. An endocardial catheter 18 is introduced into the atrium. A further catheter 20 is simultaneously introduced into the patient's body, in the present case said catheter lies on the surface 22 of the atrium and hence of the myocardium. For the ablation, an electrode 24 on the endocardial catheter 18 must be brought into the adjacency of an electrode 26 on the epicardial catheter 20. To this end, an electromagnet (not shown in FIG. 1) is arranged in the region of the electrode 24 and a permanent magnet is arranged in the region of the electrode 26. Upon excitation of the electromagnet 24, the electromagnet attracts the permanent magnet and the electrodes arrive on two opposite sides of the cardiac wall 28 in such a way that current passes substantially vertically through the cardiac wall 28 when voltage is applied between the electrodes 24 and 26. Usually, a high-frequency alternating voltage is applied, but a pulsed voltage can also be applied just as effectively. The current formed is correspondingly alternating or pulsed.

Figure 2:
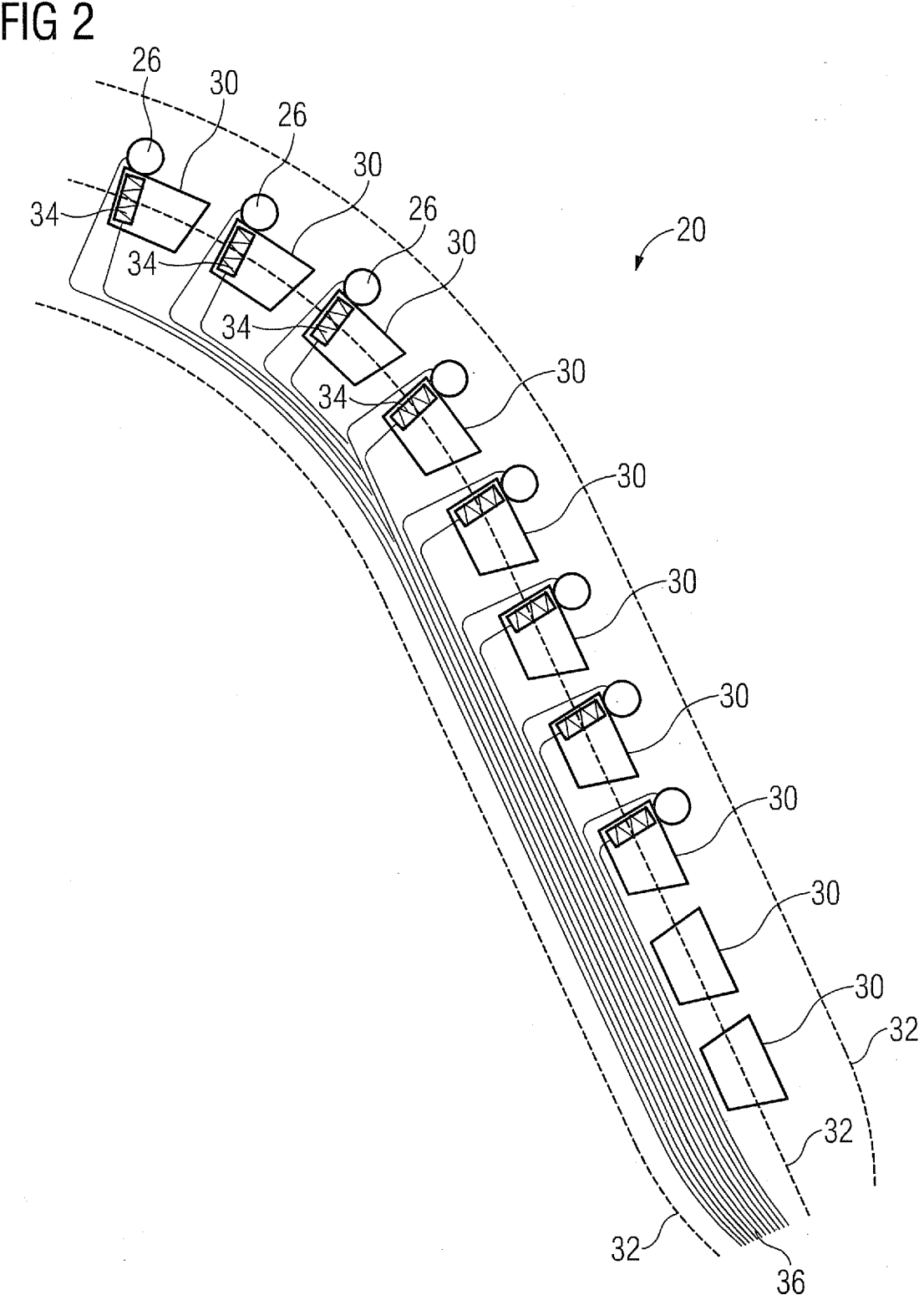
Figure 3:
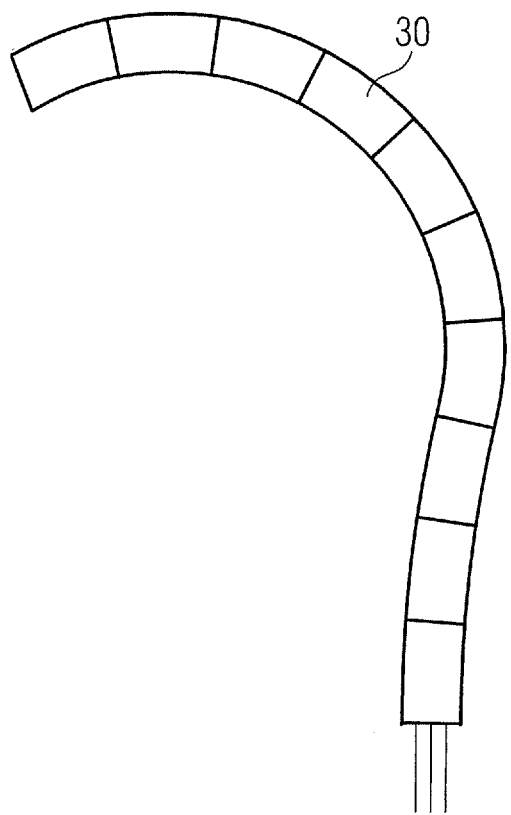

As shown in FIG. 2, the epicardial catheter 20 preferably comprises a plurality of main bodies 30 on each of which an electrode 26 is arranged. The main bodies 30 have a trapezoidal cross section, and are connected to each other by cables 32 and received in a tube-shaped container (not shown in FIG. 2). Electromagnets 34 are arranged next to the electrodes 26 on the main bodies 30. Pulling on the cables 32 results in the shape shown in FIG. 3. The trapezoidal shape of the main body 30 in particular causes the epicardial catheter 20 as a whole to be curved. The curvature can be matched to the typical shape of a pulmonary vein 16a. Pulling on the cables 32 at the correct time on the introduction of the epicardial catheter 20 causes the epicardial catheter 20 to nestle closely on the outer wall of the pulmonary vein 16a. The electrodes 26 hereby form a line. A suitable control device is used to excite electromagnet 34 after electromagnet 34 in the sequence of the main bodies 30 via respective cables 36. If the endocardial catheter 18 only comprises one electrode 24, the electrode 24 is gradually attracted to different points of the outer cardiac wall 22. If, in each case after the electromagnet 34, electric potential is applied to the associated electrodes 26, the current flows through the respective electrode 26 to the electrode 24. Optionally, it is possible for electrical potential also to be supplied to those electrodes adjacent to the electrode 24 whose associated electromagnet 34 was most recently excited.

The catheters 18 and 20 may be used to form particularly smooth lines, that is sequences of ablation points, each point of which corresponds, for example, to a main body 30 with the associated electrode 26 and the electromagnet 34.

The invention claimed is:

1. A pair of catheters, comprising:
   a first catheter for endocardial use with a first electrode; and
   a second catheter for epicardial use with a second electrode,
   wherein one of the first and the second catheters further comprises an electromagnet,
   wherein the other catheter further comprises a counter-element that can be attracted by the electromagnet,
   wherein a relative position between the electromagnet to the first or the second electrode on the one of the catheters is the same as a relative position between the counter-element to the first or the second electrode on the other catheter,
   wherein one of the first and the second catheters comprises a tube-shaped container in which a plurality of units with main bodies are arranged,
   wherein each of the main bodies comprises a trapezoidal cross section,
   wherein the main bodies are connected to each other by cables, and
   wherein the trapezoidal cross section of the main bodies results in a curved shape of the one of the first and the second catheters as a whole for matching a pulmonary vein when pulling on the cables to bring the main bodies into contact with each other.

2. The pair of catheters as claimed in claim 1, wherein the electromagnet and the counter-element are positioned so that when the counter-element is attracted by the electromagnet, the first and the second electrodes are brought into adjacency with each other.

3. The pair of catheters as claimed in claim 1, wherein the electromagnet and the counter-element are positioned so that when the counter-element is attracted by the electromagnet through a wall of a heart, the first and the second electrodes contact with opposite sides of the wall and a line connecting the first and the second electrodes passes through the wall substantially vertically.

4. The pair of catheters as claimed in claim 1, wherein each of the first and the second catheters comprises a main body with a same shape and each of the first and the second electrodes is arranged on the main body at a same position.

5. The pair of catheters as claimed in claim 1, wherein the counter-element is a ferromagnetic metal part.

6. The pair of catheters as claimed in claim 5, wherein the ferromagnetic metal part is permanently magnetized.

7. The pair of catheters as claimed in claim 1, wherein the counter-element is another electromagnet.

8. The pair of catheters as claimed in claim 1, wherein at least one of the first and the second catheters comprises a plurality of electrodes.

9. The pair of catheters as claimed in claim 8, wherein the plurality of electrodes is assigned the electromagnet or the counter-element.

10. The pair of catheters as claimed in claim 1, wherein the first and the second catheters are connected to a same voltage source.

11. The pair of catheters as claimed in claim 1, wherein each of the units comprises an electrode and an electromagnet.

12. The pair of catheters as claimed in claim 1, wherein a plurality of electromagnets are arranged on the main bodies respectively, and wherein a plurality of cables are connected to the main bodies respectively to excite the electromagnets in a sequence via the respective cables.

13. A catheter, comprising:
a tube-shaped container; and
a plurality of main bodies arranged along the container each comprising an electrode and an electromagnet,
wherein the main bodies are connected to each other by at least one cable,
wherein each of the main bodies comprises a trapezoidal cross section, and
wherein the trapezoidal cross section of the main bodies results in a curved shape of the catheter for matching an outer wall of a pulmonary vein when pulling on the at least one cable to bring the main bodies into contact with each other.

14. A method for ablating cardiac wall tissue of a heart, comprising:
inserting an endocardial catheter having a first electrode in the heart;
placing an epicardial catheter having a second electrode on the cardiac wall;
enabling a mutual attraction between the first and the second catheters by a magnetic field; and
subsequently applying a voltage to the first and the second electrodes,
wherein one of the catheters further comprises an electromagnet, and
wherein the other catheter further comprises a counter-element that can be attracted by the electromagnet,
wherein a relative position between the electromagnet to the first or the second electrode on the one of the catheters is the same as a relative position between the counter-element to the first or the second electrode on the other catheter,
wherein one of the first and the second catheters comprises a tube-shaped container in which a plurality of units with main bodies are arranged, and
wherein each of the main bodies comprises a trapezoidal cross section,
wherein the main bodies are connected to each other by cables, and
wherein the trapezoidal cross section of the main bodies results in a curved shape of the one of the first and the second catheters for matching a pulmonary vein when pulling on the cables to bring the main bodies into contact with each other.

15. The method as claimed in claim 14, wherein the voltage is initially supplied to one electrode of one of the units only and then is supplied to two adjacent electrodes of two adjacent units along the container.

* * * * *